(12) United States Patent
Ando

(10) Patent No.: US 10,257,397 B2
(45) Date of Patent: Apr. 9, 2019

(54) IMAGING APPARATUS INCLUDING LIGHT SOURCE, PHOTODETECTOR, AND CONTROL CIRCUIT

(71) Applicant: Panasonic Intellectual Property Management Co., Ltd., Osaka (JP)

(72) Inventor: Takamasa Ando, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 197 days.

(21) Appl. No.: 15/459,029

(22) Filed: Mar. 15, 2017

(65) Prior Publication Data

US 2017/0289469 A1 Oct. 5, 2017

(30) Foreign Application Priority Data

Mar. 31, 2016 (JP) .................................. 2016-070449
Dec. 20, 2016 (JP) .................................. 2016-246849

(51) Int. Cl.
*A61B 5/00* (2006.01)
*H04N 5/225* (2006.01)
(Continued)

(52) U.S. Cl.
CPC ......... *H04N 5/2256* (2013.01); *A61B 5/0059* (2013.01); *G03G 15/04* (2013.01);
(Continued)

(58) Field of Classification Search
CPC .............. H04N 2209/047; G02B 19/00; G02B 19/0004; G02B 19/0033; A61B 16/00; A61B 6/52; A61B 6/5205; A61B 5/0033
See application file for complete search history.

(56) References Cited

U.S. PATENT DOCUMENTS 6,526,298 B1 * 2/2003 Khalil .................. A61B 5/0059
  600/310
7,043,287 B1 * 5/2006 Khalil .................. A61B 5/0059
  600/310
(Continued)

FOREIGN PATENT DOCUMENTS

JP 8-103434 4/1996
JP 2003-153882 5/2003
(Continued)

*Primary Examiner* — Pankaj Kumar
*Assistant Examiner* — Timothy R Newlin
(74) *Attorney, Agent, or Firm* — McDermott Will & Emery LLP

(57) ABSTRACT

An imaging apparatus includes a light source that includes a diffusion plate and, in operation, emits, toward a subject, pulsed light that diverges; a photodetector that includes a photoelectric converter that, in operation, receives light from the subject and converts the light to an electric charge and an electric charge accumulator that, in operation, accumulates the electric charge, and, in operation, generates an electric signal based on the accumulated electric charge; and a control circuit that, in operation, controls the light source and the photodetector. The control circuit, in operation, causes the electric charge accumulator to start accumulating the electric charge when a period of time has passed after the control circuit has caused the light source to start emitting the pulsed light, and causes the electric charge accumulator to accumulate the electric charge corresponding to a component, among the light from the subject, that is scattered inside the subject.

5 Claims, 8 Drawing Sheets

(51) Int. Cl.
  *G03G 15/04* (2006.01)
  *A61B 5/026* (2006.01)
  *A61B 5/1455* (2006.01)

(52) U.S. Cl.
  CPC ............ *A61B 5/026* (2013.01); *A61B 5/0261* (2013.01); *A61B 5/1455* (2013.01); *A61B 5/7207* (2013.01); *A61B 5/7235* (2013.01)

(56) References Cited

U.S. PATENT DOCUMENTS

| | | | | |
|---|---|---|---|---|
| 2007/0201130 | A1* | 8/2007 | Fujinoki | A61B 5/0059 359/398 |
| 2008/0208018 | A1* | 8/2008 | Ridder | A61B 5/0059 600/322 |
| 2009/0005685 | A1* | 1/2009 | Nagae | A61B 5/0059 600/459 |
| 2009/0009595 | A1* | 1/2009 | Ishiwata | A61B 1/00165 348/68 |
| 2009/0018414 | A1* | 1/2009 | Toofan | A61B 5/0059 600/310 |
| 2009/0039241 | A1* | 2/2009 | Ueki | A61B 5/0059 250/227.14 |
| 2011/0144505 | A1* | 6/2011 | Yamamoto | A61B 5/0064 600/476 |
| 2012/0041290 | A1* | 2/2012 | Perelman | A61B 5/0062 600/326 |
| 2012/0257034 | A1* | 10/2012 | Shimokita | A61B 5/0059 348/77 |
| 2017/0231513 | A1* | 8/2017 | Presura | A61B 5/0066 600/301 |

FOREIGN PATENT DOCUMENTS

| | | |
|---|---|---|
| JP | 2007-260123 | 10/2007 |
| JP | 2008-039635 | 2/2008 |
| JP | 2010-175435 | 8/2010 |

\* cited by examiner

FIG. 9

| θ [deg] | R [mm] | | | | | | | |
|---|---|---|---|---|---|---|---|---|
| | 25 | 50 | 100 | 150 | 200 | 250 | 300 | 350 | 400 |
| 2 | 15.1 | 40.1 | 90.1 | 140.1 | 190.1 | 240.1 | 290.1 | 340.1 | 390.1 |
| 4 | −20.7 | 4.3 | 54.3 | 104.3 | 154.3 | 204.3 | 254.3 | 304.3 | 354.3 |
| 6 | −32.7 | −7.7 | 42.3 | 92.3 | 142.3 | 192.3 | 242.3 | 292.3 | 342.3 |
| 8 | −38.7 | −13.7 | 36.3 | 86.3 | 136.3 | 186.3 | 236.3 | 286.3 | 336.3 |
| 10 | −42.3 | −17.3 | 32.7 | 82.7 | 132.7 | 182.7 | 232.7 | 282.7 | 332.7 |
| 15 | −47.2 | −22.2 | 27.8 | 77.8 | 127.8 | 177.8 | 227.8 | 277.8 | 327.8 |
| 20 | −49.6 | −24.6 | 25.4 | 75.4 | 125.4 | 175.4 | 225.4 | 275.4 | 325.4 |
| 25 | −51.1 | −26.1 | 23.9 | 73.9 | 123.9 | 173.9 | 223.9 | 273.9 | 323.9 |
| 30 | −52.2 | −27.2 | 22.8 | 72.8 | 122.8 | 172.8 | 222.8 | 272.8 | 322.8 |
| 35 | −52.9 | −27.9 | 22.1 | 72.1 | 122.1 | 172.1 | 222.1 | 272.1 | 322.1 |
| 40 | −53.5 | −28.5 | 21.5 | 71.5 | 121.5 | 171.5 | 221.5 | 271.5 | 321.5 |
| 45 | −54.0 | −29.0 | 21.0 | 71.0 | 121.0 | 171.0 | 221.0 | 271.0 | 321.0 |
| 50 | −54.4 | −29.4 | 20.6 | 70.6 | 120.6 | 170.6 | 220.6 | 270.6 | 320.6 |
| 55 | −54.7 | −29.7 | 20.3 | 70.3 | 120.3 | 170.3 | 220.3 | 270.3 | 320.3 |
| 60 | −55.1 | −30.1 | 19.9 | 69.9 | 119.9 | 169.9 | 219.9 | 269.9 | 319.9 |
| 65 | −55.3 | −30.3 | 19.7 | 69.7 | 119.7 | 169.7 | 219.7 | 269.7 | 319.7 | ically
IMAGING APPARATUS INCLUDING LIGHT SOURCE, PHOTODETECTOR, AND CONTROL CIRCUIT

BACKGROUND

1. Technical Field

The present disclosure relates to imaging apparatuses.

2. Description of the Related Art

In the field of biometry, materials analysis, and so on, a method is used in which a subject is irradiated with light and information on the inside of the subject is acquired from information on the light that has been transmitted through the inside of the subject. In this method, there arises a problem that a component reflected from the surface of the subject and a component scattered directly underneath the surface are mixed into the aforementioned light. In particular, in biometry, the intensity of a surface reflection component and a subsurface scattering component is four to five orders of magnitude larger than the intensity of a component scattered inside an organism, and it is desirable that these surface reflection component and subsurface scattering component be removed as much as possible in order to acquire the component scattered inside the organism. In the field of biometry, for example, methods of acquiring only the desired information on the inside by removing the aforementioned components include a method disclosed in Japanese Unexamined Patent Application Publication No. 8-103434. Japanese Unexamined Patent Application Publication No. 8-103434 discloses a method in which measurement is carried out in a state in which a light source and a photodetector are in tight contact with a site to be measured with a certain space being provided between the light source and the photodetector.

SUMMARY

In one general aspect, the techniques disclosed here feature an imaging apparatus that includes a light source that includes a diffusion plate and, in operation, emits pulsed light toward a subject, the pulsed light diverging at a divergence angle greater than 0 degrees; a photodetector including a photoelectric converter that, in operation, receives light from the subject and converts the light to an electric charge and an electric charge accumulator that, in operation, accumulates the electric charge, the photodetector, in operation, generating an electric signal based on the electric charge accumulated in the electric charge accumulator; and a control circuit that, in operation, controls the light source and the photodetector. The control circuit, in operation, causes the electric charge accumulator to start accumulating the electric charge when a predetermined period of time has passed after the control circuit has caused the light source to start emitting the pulsed light, and thus causes the electric charge accumulator to accumulate the electric charge corresponding to a component, among the light from the subject, that is scattered inside the subject. The pulsed light satisfies the following expression: $81.5 \leq R + d/(2 \tan \theta)$, where R (mm) is a distance from the diffusion plate to the subject, $\theta$ (degree) is the divergence angle, and d (mm) is a spot size of the pulsed light on the diffusion plate.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9 illustrates an example of values obtained by subtracting the right-hand side from the left-hand side of the expression (13).

DETAILED DESCRIPTION

Figure 1:
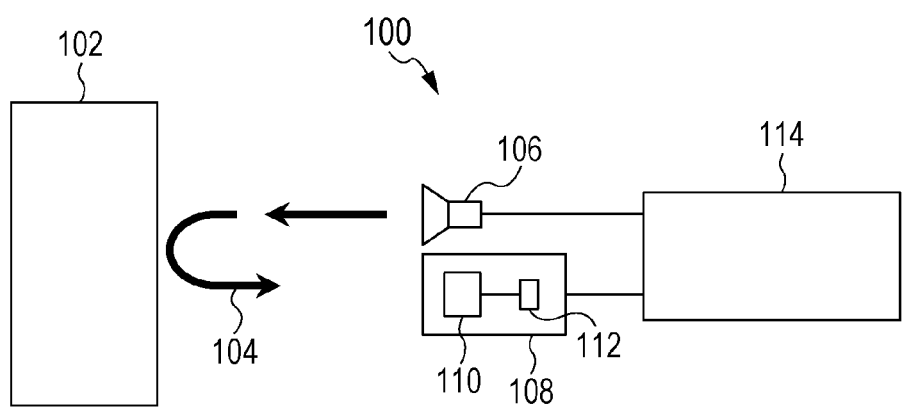
FIG. 1 is a schematic diagram illustrating an imaging apparatus according to a first embodiment.

According to the detailed study by the inventor of the present application, it is possible to reduce the proportion of the subsurface scattering component contained in a detection signal and to increase the detection amount of the scattered component of light that has reached the brain with the method disclosed in Japanese Unexamined Patent Application Publication No. 8-103434. However, this method requires that the irradiation point and the detection point be spaced apart by 3 cm, and the spatial resolution of the obtained brain activity distribution may decrease.

In the meantime, an image sensor capable of high-speed imaging for measuring the distance to a subject through a time-of-light (TOF) system has been developed in recent years. Such an image sensor has a high time division resolution. Thus, by controlling the shutter of the image sensor at high speed, a component scattered inside the brain may be detected while greatly reducing the surface reflection component and the subsurface scattering component having a high intensity. Specifically, in a case in which an organism is irradiated with pulsed light and the light reflected by the organism is imaged, the light reflected near the surface of the organism has a relatively shorter optical path and thus reaches the image sensor at an earlier timing, whereas the light reflected inside the organism has a relatively longer optical path and thus reaches the image sensor at a later timing. Therefore, by adjusting the shutter such that the trailing end portion of the pulsed light returning to the image sensor is detected, the component scattered inside the brain having a relatively longer optical path length and having a time delay can be detected efficiently. This method of detecting components with a temporal separation makes it possible to detect a brain signal directly underneath the irradiation point, and thus it is considered that the brain activity distribution with a higher resolution can be acquired as compared to the method disclosed in Japanese Unexamined Patent Application Publication No. 8-103434.

However, when a signal from a subject is detected in a contactless manner, movement of the subject leads to a change in the amount of an optical signal detected by the sensor, which results in an output of an erroneous detection value. In particular, when a very tiny amount of a component scattered inside the brain is to be detected as in the cerebral blood flow measurement, an influence of a noise component associated with movement is large, and the S/N ratio in the detection of the component scattered inside the brain is reduced. In view of the issue described above, the inventor of the present application has conceived of an imaging apparatus having a novel structure. The overview of the imaging apparatus according to the present disclosure is as follows.

An imaging apparatus according to an aspect of the present disclosure includes a light source that includes a diffusion plate and, in operation, emits pulsed light toward a subject, the pulsed light diverging at a divergence angle greater than 0 degrees; a photodetector including a photoelectric converter that, in operation, receives light from the subject and converts the light to an electric charge and an electric charge accumulator that, in operation, accumulates the electric charge, the photodetector, in operation, generating an electric signal based on the electric charge accumulated in the electric charge accumulator; and a control circuit that, in operation, controls the light source and the photodetector. The control circuit, in operation, causes the electric charge accumulator to start accumulating the electric charge when a predetermined period of time has passed after the control circuit has caused the light source to start emitting the pulsed light, and thus causes the electric charge accumulator to accumulate the electric charge corresponding to a component, among the light from the subject, that is scattered inside the subject. The pulsed light satisfies the following expression: $81.5 \leq R + d/(2 \tan \theta)$, where R (mm) is a distance from the diffusion plate to the subject, θ (degree) is the divergence angle, and d (mm) is a spot size of the pulsed light on the diffusion plate. In the above, R, d, θ>0 holds true. The distance from the diffusion plate to the subject may be equal to or greater than 25 mm, and may be equal to or less than 400 mm.

The imaging apparatus according to the aspect of the present disclosure may further include a divergence angle adjusting mechanism that adjusts the divergence angle.

The imaging apparatus according to the aspect of the present disclosure may further include a pattern projector that, in operation, converts the pulsed light to light including a desired pattern.

In the imaging apparatus according to the aspect of the present disclosure, the electric signal may include a predetermined offset component, and the control circuit may, in operation, remove the predetermined offset component from the electric signal.

An imaging apparatus according to another aspect of the present disclosure includes a light source that emits pulsed light toward a subject; a photodetector including a photoelectric converter and an electric charge accumulator that accumulates an electric charge generated by the photoelectric converter, the photodetector outputting an electric signal upon the electric charge being read out; and a control circuit. When a distance between the subject and the light source takes a first value, the control circuit causes the electric charge accumulator to start accumulating an electric charge upon a predetermined period of time having passed after the control circuit has caused the light source to start emitting the pulsed light and thus generates a first electric signal. When the distance between the subject and the light source takes a second value, which is different from the first value, the control circuit causes the electric charge accumulator to start accumulating an electric charge upon a predetermined period of time having passed after the control circuit has caused the light source to start emitting the pulsed light and thus generates a second electric signal. The predetermined period of time is a timing at which an intensity of the first electric signal becomes equal to an intensity of the second electric signal.

A difference Δr between the first value r1 and the second value may satisfy the following expression.

$$\left| \frac{-1}{\frac{r_1}{2\Delta r} + 1} + \exp\left(\alpha \frac{2\Delta r}{c}\right) - 1 \right| < |k|$$

In the above, α is an attenuation coefficient of a phase change of the intensity of an electric signal of returning light from the subject, and k is a ratio of a desired amount of change in the electric signal relative to the initial intensity of the electric signal.

A difference Δr between the first value r1 and the second value may satisfy the following expression.

$$\left| \frac{-1}{\frac{r_1}{2\Delta r} + 1} + \exp\left(\frac{3\Delta r}{c}\right) - 1 \right| < 0.1$$

When the first value r1 is 100 cm, 50 cm, 25 cm, 20 cm, 16 cm, 15 cm, and 10.5 cm, the difference Δr between the first value and the second value may be, respectively, no less than 0.6 cm nor more than 1.2 cm, no less than 0.7 cm nor more than 1.4 cm, no less than 1.1 cm nor more than 2.3 cm, no less than 1.4 cm nor more than 2.7 cm, no less than 1.7 cm nor more than 3.3 cm, no less than 2.3 cm nor more than 4.6 cm, and no less than 3 cm nor more than 5 cm.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or a large scale integration (LSI). The LSI or IC can be integrated into one chip or can be a combination of plural chips. For example, functional blocks other than a memory may be integrated into one chip. The name used herein is LSI or IC, but it may also be called a system LSI, VLSI (very large scale integration), or ULSI (ultra large scale integration)

depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Furthermore, it is also possible that all or a part of the functions or operations of the circuit, unit, device, part or portion is implemented by executing software. In such a case, the software is recorded on one or more non-transitory recording media such as a ROM, an optical disk, or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Hereinafter, embodiments will be described in concrete terms with reference to the drawings.

First Embodiment

Configuration of Imaging Apparatus

First, a configuration of an imaging apparatus 100 according to a first embodiment will be described with reference to FIG. 1.

The imaging apparatus 100 includes a light source 106, a photodetector 108 that includes a photoelectric converter 110 and an electric charge accumulator 112, and a control circuit 114. The light source 106 emits light 104, which is pulsed light, toward a subject 102. The light 104 that has reached the subject 102 experiences an optical phenomenon such as reflection, diffusion, absorption, or scattering at the surface of and inside the subject 102, and then a portion of that light 104 reaches the photoelectric converter 110 in the photodetector 108. The control circuit 114 includes a memory having a program stored therein and an arithmetic unit. The control circuit 114 reads out and executes the program stored in the memory. Thus, the control circuits 114 causes the electric charge accumulator 112 to start accumulating an electric charge upon a predetermined period of time having passed after the control circuit 114 has caused the light source 106 to start emitting the light 104 and controls the generation of an electric signal in accordance with the procedure specified by the program. When the subject 102 is an organism, a portion of the light 104 emitted by the light source 106 reaches the inside of the subject 102. The light 104 that has been scattered inside the subject 102 experiences a time delay due to the scattering, and thus the pulsed light that returns to the imaging apparatus 100 includes a tail composed of a component of the light 104 that has been scattered inside the subject 102. Information on a portion deep inside the subject 102 (e.g., a component that has reached the brain in the measurement of a head) has a longer optical path length than the light scattered near the surface of the subject 102. Therefore, the proportion of the information on a portion deep inside the organism (component scattered inside the brain) included in a detection signal can be increased by starting a shutter at a timing at which the tail that is temporally behind the trailing end of the returning pulsed light reaches the imaging apparatus 100. Herein, starting a shutter means to start accumulating an electric charge in the electric charge accumulator 112. In a case in which the sensitivity is not sufficient in a single instance of pulsed light measurement, the aforementioned operation is repeated a plurality of times, and the amount of detection light is amplified through integration. For example, the operation is repeated several hundred to several million times.

The light source 106 is constituted, for example, by a fluorescent lamp, a light-emitting diode (LED), a laser diode (LD), or the like. In order to separate the information on a portion deep inside the subject 102 from the information on the vicinity of the surface, it is desirable that the trailing end of the pulsed light fall sharply. Thus, a light source that emits a laser beam, such as an LD, may be used. When the oxygenation index of the blood flow of the subject 102 is to be measured, the light source 106 that emits near-infrared light that can be transmitted through the inside of the organism to a certain degree is used, for example. Furthermore, in order to detect a change in the concentration of oxyhemoglobin and deoxyhemoglobin, the light source 106 may emit two-wavelength light 104. For example, the light source 106 emits the light 104 at a wavelength of around 750 nm and the light 104 at a wavelength of around 850 nm. In this case, the photodetector 108 may include a plurality of electric charge accumulators 112 for a single photoelectric converter 110 and accumulate electric charges in the respective electric charge accumulators 112 by subjecting the two-wavelength light to time division. Providing a plurality of electric charge accumulators 112 makes it possible to acquire a plurality of different pieces of information within a single frame at substantially the same time. In addition, aside from the information on the different wavelengths, information on different polarization states, information on different intensities, or information on different phase differences can be acquired at the same time. For such a photodetector 108, the imaging apparatus disclosed in Japanese Unexamined Patent Application Publication No. 2008-89346 can be used, for example.

The photodetector 108 used in the imaging apparatus 100 includes the photoelectric converter 110 and the electric charge accumulator 112. The photodetector 108 may be a photodiode, a photomultiplier tube, a charge-coupled device (CCD) or complementary metal-oxide semiconductor (CMOS) image sensor, a single photon counting device, or an amplifying image sensor (electron multiplying charge-coupled device (EMCCD), intensified charge-coupled device (ICCD)).

Figure 2:
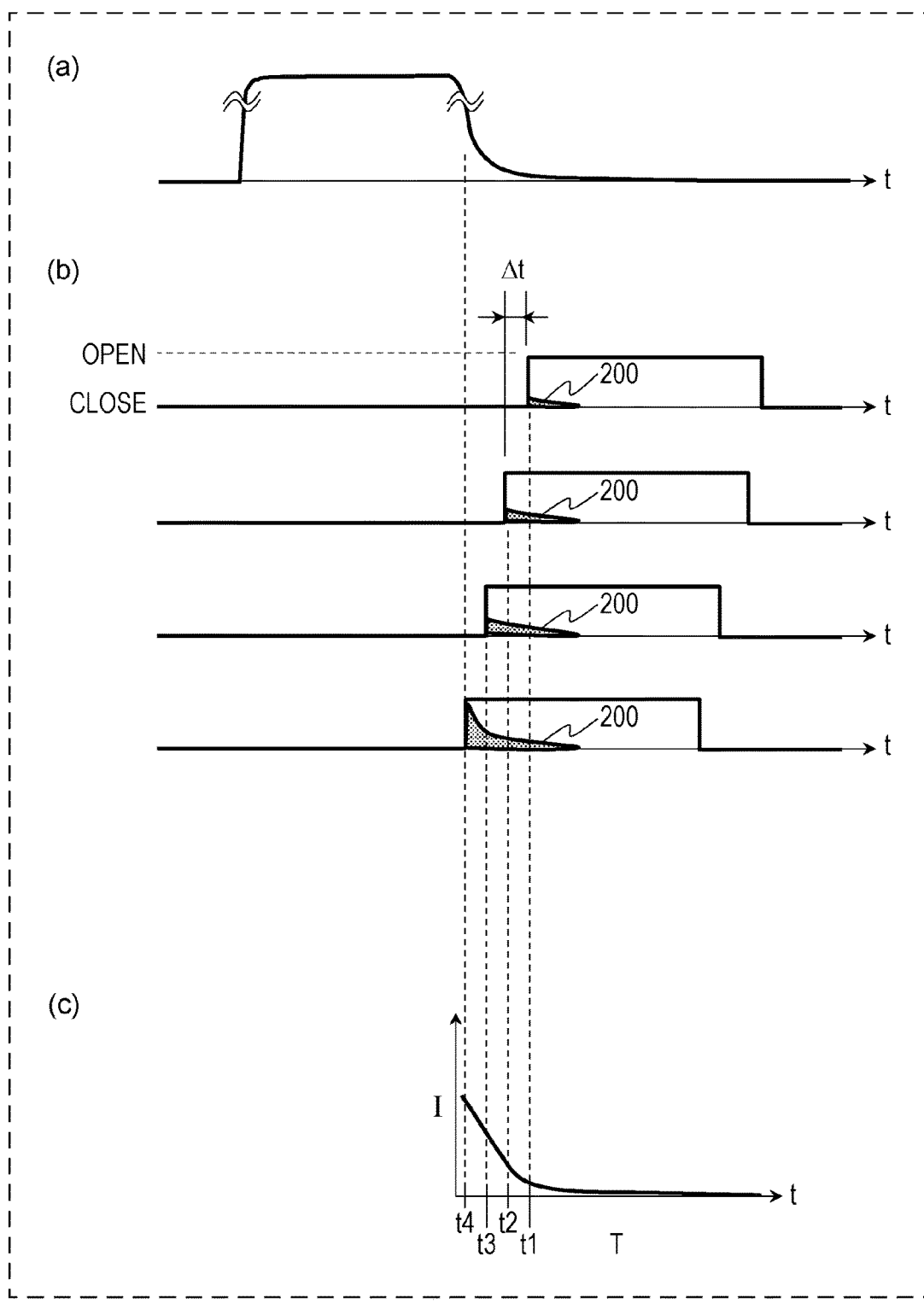
FIG. 2 illustrates a time response waveform of an optical signal that reaches a photodetector, a relationship between a shutter timing and a detected optical signal, and a relationship between a shutter start phase and the detection intensity of a detected optical signal.

A waveform (a) illustrated in FIG. 2 is a time response waveform of an optical signal that reaches the photodetector 108. When the pulse duration of the light source 106 is short to a certain degree, the waveform (a) can be regarded as the optical path length distribution. In other words, light with a longer optical path length reaches the photodetector 108 with a greater time delay and is thus detected at a relative large t (later time). That is, the time response waveform has a spread corresponding to the optical path length distribution.

Waveforms (b) illustrated in FIG. 2 represent shutter timings when a shutter start phase T falls at t1, t2, t3, and t4 (t1>t2>t3>t4). The shutter start phase T is a time difference between the emission timing of the pulsed light by the light source 106 and the timing at which the shutter of the photodetector 108 is started. In a graph (c) illustrated in FIG. 2, the horizontal axis represents the shutter start phase T, and the vertical axis represents the detection intensity I of the detected optical signal. As illustrated in the waveforms (b) and the graph (c), the detection intensity I of a detected optical signal 200 increases as the shutter start phase T is brought temporally forward. The setting of the shutter start phase T may be adjusted by the emission start time of the illumination or may be adjusted by the electric charge accumulation start time of the sensor.

Figure 3A:
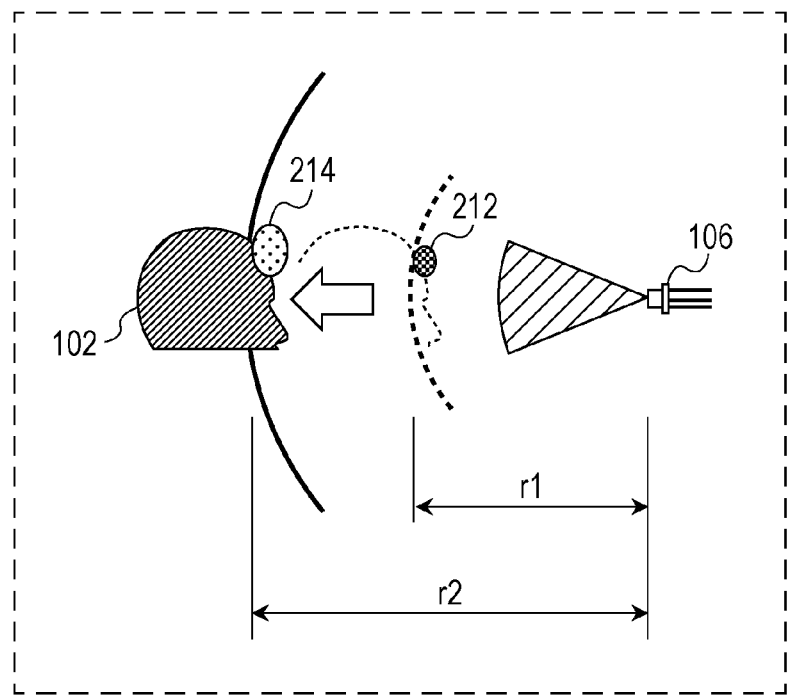
FIG. 3A illustrates a change in the density of irradiation light associated with movement of a subject.

FIG. 3A illustrates a change in the density of irradiation light associated with the movement of the subject 102. In a case in which the light source 106 emits radiation light having a spread, the illuminance (=optical intensity density) decreases as the distance from the light source 106 to the subject 102 increases. Therefore, when the subject 102 has moved to the position of a distance r2, which is greater than a distance r1, from the position of the distance r1, the optical intensity density of irradiation light 214 on the subject 102 when the subject 102 is at the position of the distance r2 is smaller than the optical intensity density of irradiation light 212 on the subject 102 when the subject 102 is at the position of the distance r1.

Figure 3B:
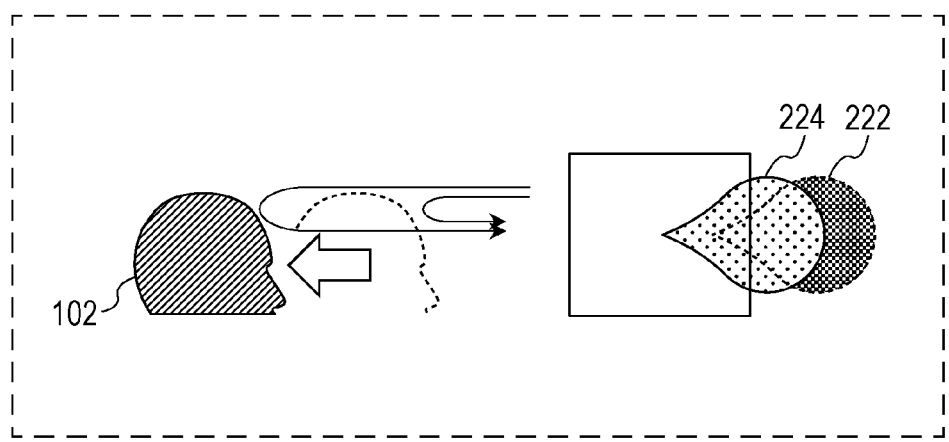
FIG. 3B illustrates a time delay of returning light with respect to the same movement as that of FIG. 3A.

In the meantime, FIG. 3B illustrates a time delay of returning light with respect to the same movement of the subject 102 as that of FIG. 3A. When the subject 102 has moved from the position of the distance r1 to the position of the distance r2, the flight distance of the light that reaches the subject 102 from the light source 106 and returns to the light source 106 is greater for returning light 224 obtained when the subject 102 is at the position of the distance r2 than for returning light 222 obtained when the subject 102 is at the position of the distance r1. Therefore, the returning light 224 reaches the photodetector 108 later than the returning light 222 does. In other words, if the shutter is started at a constant timing after the light source 106 has emitted light, the amount of detected light increases when the subject 102 moves from the position of the distance r1 to the position of the distance r2. It is to be noted that the rectangular frame illustrated in FIG. 3B indicates the duration for which the shutter is open.

The phenomena illustrated in FIGS. 3A and 3B both serve as factors for an error in the detection signal with respect to the movement of the subject 102, but these phenomena have a negative correlation. In other words, the phenomena illustrated in FIGS. 3A and 3B are factors for errors that are opposite to each other with respect to the movement of the subject 102. Thus, by controlling the timing of the shutter such that these phenomena cancel out each other, the influences of the phenomena illustrated in FIGS. 3A and 3B associated with the movement of the subject 102 can cancel out each other.

The illuminance of the irradiation light from the light source 106 on the subject 102 is inversely proportional to the square of the distance between the light source 106 and the subject 102, and thus the intensity of the detected optical signal is also inversely proportional to the square of the distance between the light source 106 and the subject 102. The intensity of an optical signal detected when the distance 1 (initial distance) between the light source 106 and the subject 102 is $r_1$ is represented by $I_1$. Then, the intensity $I^{ill}$ of an optical signal detected when the distance between the light source 106 and the subject 102 is r is expressed by the following expression (1).

$$I^{ill} = I_1 \frac{r_1^2}{r^2} \quad (1)$$

Therefore, the amount $\Delta I^{ill}$ of change in the detected optical signal resulting from a change in the illuminance of the irradiation light on the subject 102 can be expressed by the following expression (2).

$$\Delta I^{ill} = -\frac{2I_1}{r_1} \Delta r \quad (2)$$

In the above, $\Delta r$ is the amount of movement in the z-direction (the direction from the light source 106 toward the subject 102). In other words, $\Delta I^{ill}$ is inversely proportional to the initial distance $r_1$.

On the other hand, the amount of change in the detected optical signal resulting from a change in the flight distance of the returning light from the subject 102 is dependent on the time response waveform of the returning light that reaches the photodetector 108. It is known that, when light is transmitted through a scattering medium such as an organism, the time response of an exponential intensity is observed in accordance with the Lambert-Beer's formula. Thus, the intensity $I^{dis}$ of the optical signal detected as a function of the time of flight (shutter start phase) t of the returning light is expressed by the following expression (3).

$$I^{dis} = I_1 \exp\{-\alpha(t-t_1)\} \quad (3)$$

In the above, $t_1$ is the initial phase, and a is the attenuation coefficient that is dependent on the absorption coefficient and the scattering coefficient of the subject 102 and the attenuation of the pulsed light emitted by the light source 106, or in other words, $\alpha$ is the attenuation coefficient of the detection intensity of the returning light. For example, $\alpha$ is the coefficient when the waveform in the graph (c) illustrated in FIG. 2 is expressed in an exponential function.

The amount $\Delta I^{dis}$ of change in the detected optical signal resulting from a change in the flight distance of the returning light from the subject 102 can be expressed by the following expression (4).

$$\Delta I^{dis} = -\frac{dI_1(t_1)}{dt} \frac{2\Delta r}{c} \quad (4)$$

In the above, $\Delta t$ is $-2\Delta r/c$, and c is the speed of light. On the basis of the expression (4), it can be seen that $\Delta I^{dis}$ is proportional to the slope (the slope of the graph (c) illustrated in FIG. 2) of the phase change of the optical signal detection intensity.

Therefore, in order to suppress a change in the detected optical signal associated with the movement of the subject 102, the phase that satisfies the following expression (5) may be set as the initial phase.

$$\Delta I^{ill} = -\Delta I^{dis} \quad (5)$$

In other words, the phase position that achieves the following expression (6) may be set.

$$\frac{I_1}{r_1} = -\frac{dI_1(t_1)}{dt} \frac{1}{c} \quad (6)$$

Figure 4A:
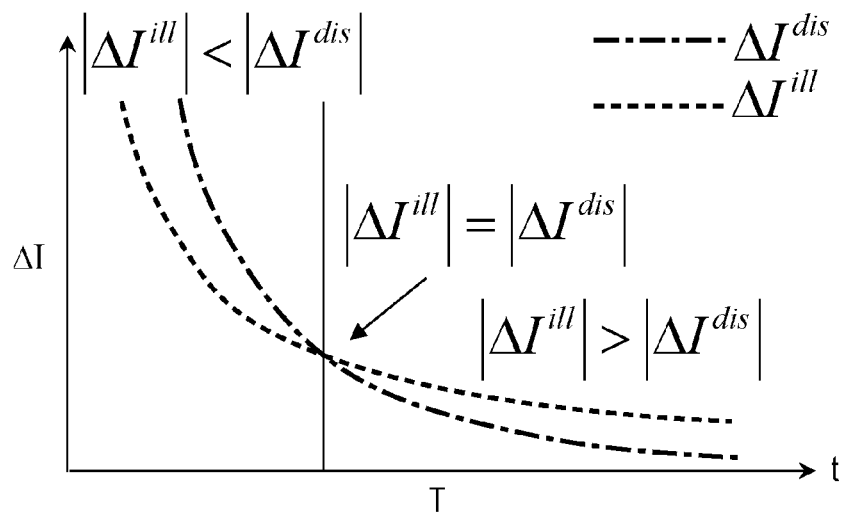
FIG. 4A illustrates a relationship between a shutter start phase and an amount of change in a detected optical signal with respect to movement of a subject.

FIG. 4A illustrates a relationship between the shutter start phase T and an amount $\Delta I$ of change in the detected optical signal with respect to the movement of subject 102. $\Delta I^{ill}$ is the absolute value of the amount of change in the detected optical signal resulting from a change in the illuminance of the irradiation light on the subject 102, and $\Delta I^{dis}$ is the absolute value of the amount of change in the detected optical signal resulting from a change in the flight distance of the returning light from the subject 102. For example, when the shutter start phase is too late (e.g., corresponding to t=t1 in the graph (c) illustrated in FIG. 2), the detected light is light at a position that is spaced apart from the trailing end of the returning light and at which the change in the quantity of light is small, which thus leads to $\Delta I^{ill} > \Delta I^{dis}$. In the meantime, when the shutter start phase is too early (e.g., corresponding to t=t4 in the graph (c) illustrated in FIG. 2), the detected light is light at a position that is spaced apart from the trailing end of the returning light and at which the change in the quantity of light is small, which thus leads to $\Delta I^{ill} < \Delta I^{dis}$.

Figure 4B:
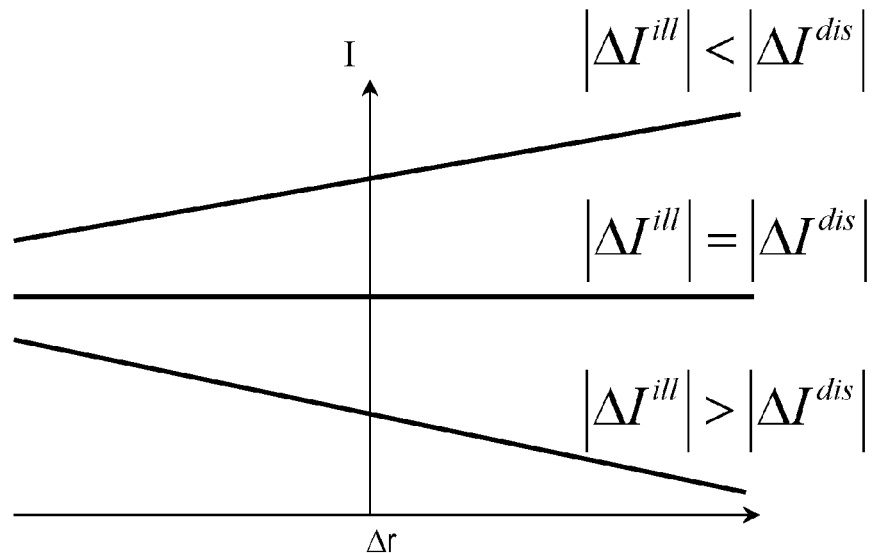
FIG. 4B illustrates a relationship between movement of a subject and the intensity of a detected optical signal.

FIG. 4B illustrates a relationship between the amount Δr of movement of the subject 102 and the intensity I of the detected optical signal. By setting the shutter start phase appropriately, the intensity of the detected optical signal can be kept constant even when the subject 102 moves. Specifically, in a case in which the subject 102 is measured at the initial phase that satisfies the expression (5) or the expression (6), the intensity of the optical signal obtained when the distance from the light source 106 to the subject 102 is r1 (first value) is equal to the intensity of the optical signal obtained when the distance from the light source 106 to the subject 102 is r2 (second value). Therefore, the electric signal output from the photodetector 108 when the distance is r1 is equal to the electric signal output when the distance is r2.

Setting of Initial Phase

The initial phase can be set through a method in which the determination is made by calibration or a method in which a table prepared in advance is used. The method that uses the calibration can be further divided into a passive system and an active system. In the passive system, the subject 102 is moved away from the light source 106 or, if the subject 102 is a human being, the subject 102 is instructed to move away from the light source 106. Then, the shutter start phase is brought temporally forward if the movement results in a decrease in the quantity of detected light, or the shutter start phase is delayed if the movement results in an increase in the quantity of detected light. This operation is repeated efficiently with the use of the Newton's method, a bisection method, or the like, and the calibration is terminated when there is no change in the quantity of light. The same applies in the case in which the subject 102 is brought closer to the light source 106. In the active system, the subject 102 is moved freely (or is allowed to move freely, and the direction of the movement of the subject 102 is detected by measuring the distance on the device side. Thus, it is determined whether the subject 102 is moving away from or closer to the light source 106. Then, the shutter start phase is determined in accordance with the increase or decrease in the quantity of detected light. The measurement of the distance can be achieved by driving the control circuit 114 in the time-of-flight (TOF) mode with the use of the pulsed light of the imaging apparatus or by separately providing a distance measuring device such as a stereo range finding camera.

In the case of the method that uses a table prepared in advance, a table indicating the relationship between the optimal shutter start phase and the distance between the light source 106 and the subject 102 is created in advance in accordance with the optical characteristics of the subject 102 and the waveform of the returning light. Then, the distance to the subject 102 is measured, and the shutter start phase is determined uniquely by referring to the table. This method makes it unnecessary to carry out the calibration in advance.

In a case in which there are a plurality of subjects to be measured, when the materials and the optical characteristics of the subjects 102 are similar to one another, the initial phase may be determined on the basis of one of the subjects 102, and the same setting may be applied to the other subjects 102. On the other hand, when the materials of the subjects 102 greatly differ from one another, or in other words, when the scattering coefficient and the absorption coefficients greatly differ among the subjects 102, the phase change of the optical signal intensity (the change in the slope of the trailing end of the returning light) also differs among the subjects 102. Thus, the initial phase may be determined, for example, for each of the subjects 102.

Permissible Movement Range

Next, the permissible range of movement that can be corrected will be considered. When the amount of change in the detection signal associated with movement is smaller than the amount of change in the signal to be detected (e.g., blood flow change reaction associated with a task from a calm state), the S/N ratio with respect to the movement is equal to or greater than 1, and the measurement is possible. When the amount of change in the signal to be detected is represented by $\Delta I^{task}$, the relationship of the following expression (7) can be obtained as a condition in which the S/N ratio is equal to or greater than 1.

$$|\Delta I^{ill} + \Delta I^{dis}| < |\Delta I^{task}| \tag{7}$$

In the expression (2) and the expression (4), $\Delta I^{ill}$ and $\Delta I^{dis}$ are both derived from the derivatives, and thus the applicable range is limited to the movement within the range in which linear approximation holds, but the amount is calculated again with accuracy from the expression (1) and the expression (3) in order to obtain the permissible error.

When the distance between the light source 106 and the subject 102 has changed from the initial distance $r_1$ to $r_2$, the amount $\Delta I^{ill}$ of change in the detected optical signal resulting from a change in the illuminance of the irradiation light on the subject 102 is expressed by the following expression (8) on the basis of the expression (1).

$$\Delta I^{dis} = I_1 \left( \frac{r_1^2}{r_2^2} - 1 \right) \tag{8}$$

$$= I_1 \frac{r_1^2 - (r_1 + \Delta r)^2}{(r_1 + \Delta r)^2}$$

$$\cong I_1 \frac{-1}{\frac{r_1}{2\Delta r} + 1}$$

In the meantime, the amount $\Delta I^{dis}$ of change in the detected optical signal resulting from a change in the flight distance of the returning light from the subject 102 is expressed by the following expression (9).

$$\Delta I^{dis} = I_1 \{\exp(-\alpha \Delta t) - 1\} \tag{9}$$

$$= I_1 \left\{ \exp\left(\alpha \frac{2\Delta r}{c}\right) - 1 \right\}$$

When the amount $\Delta I^{task}$ of change in the signal to be detected is k times the initial intensity $I_1$ of the detected optical signal, the following expression (10) holds true.

$$\Delta I^{task} = k I_1 \tag{10}$$

Therefore, when the expression (8) and the expression (9) are substituted into the expression (7), the following expression (11) is obtained.

$$\left| \frac{-1}{\frac{r_1}{2\Delta r} + 1} + \exp\left(\alpha \frac{2\Delta r}{c}\right) - 1 \right| < |k| \qquad (11)$$

As long as Δr is in the range that satisfies the expression (11), the S/N ratio exceeds 1, and the movement correction can be effective. In other words, in a case in which the initial phase that satisfies the expression (5) or the expression (6) is used and the subject 102 is measured with the distance from the light source 106 to the subject 102 being the distance r1 and the distance r2 that differ from each other, as long as the difference Δr between r1 and r2 satisfies the expression (11), the amount of change in the signal to be detected obtained from the subject 102 exceeds the amount of change in the detected signal associated with the movement of the subject 102, and the effective measurement can be carried out.

According to the experimental study by the inventor of the present application, the attenuation coefficient α of the returning light when the light source 106 irradiates an organism with rectangular pulsed light is 1.5 [1/ns]. For example, the initial distance $r_1$ is 16 cm, the proportion k of the amount of change in the signal with respect to a task is 0.1, and the speed of light c is 300,000,000 m/s. Then, the permissible range Δr of the movement that can be corrected is ±3.3 cm. The relationship between the initial distance r1 and the permissible movement range Δrb is illustrated below. The initial distance r1 is set to 5-100 cm, which is a typical measurement range.

TABLE 1

| r1 [cm] | Δra [cm] | Δrb [cm] |
|---|---|---|
| 100.0 | 0.6 | 1.2 |
| 50.0 | 0.7 | 1.4 |
| 25.0 | 1.1 | 2.3 |
| 20.0 | 1.4 | 2.7 |
| 16.0 | 1.7 | 3.3 |
| 15.0 | 1.7 | 3.5 |
| 10.0 | 2.3 | 4.6 |
| 5.0 | 3.0 | 5.9 |

A desired signal change can be detected with respect to the movement of the subject 102 within the range indicated in Table 1. For example, while the difference between the distance r1 and the distance r2 in FIG. 3A is within the range of no less than Δrb/2 (=Δra), which is half the limit value, nor more than Δrb, a comparison between the optical detection intensity at the distance r1 and the optical detection intensity at the distance r2 makes it possible to confirm that the S/N ratio is equal to or greater than 1.

When the subject 102 has moved greatly so as to exceed the range in the expression (11) or in Table 1, the initial value may be reset. Whether or not the movement has exceeded the permissible range can be determined by periodically measuring the distance to the subject 102 through TOF during the measurement period with the use of the imaging apparatus 100 capable of TOF or by separately providing a distance detecting mechanism of stereo range finding or the like. When the initial value is reset, the measurement may be continued with a new initial value, or in a case in which the subject 102 is a human being, the measurement may be restarted from the beginning or may be prompted as such.

When the scattering inside the subject 102 is small and the optical signal of the vicinity of the surface of the subject 102 is detected, attenuating the trailing end of the pulsed light emitted by the light source 106 as in the waveform (a) illustrated in FIG. 2 in advance is also effective in correcting the movement of the subject 102. When the trailing end is attenuated in advance, even if there is little time delay associated with the scattering in the subject 102, the attenuated trailing end can be used to adjust the amount of increase or decrease in the detection signal caused by the time delay of the optical signal associated with the movement of the subject 102.

Although the present embodiment concerns with the correction of the movement in the z-direction, the corrections of x- and y-shift of the subject 102 and the corrections of panning and tilting may also be combined. For these movements, motion tracking through a camera image, acceleration measurement provided on the subject 102, or the like may be used. When a camera image is used together with an image of the imaging apparatus 100, the number of sensing devices can be reduced. A three-dimensional movement of the subject 102 can be corrected through a matrix operation on the detected movement vector. The correction in the z-direction can also be combined with the correction through the motion tracking. In this case as well, optimizing the initial phase position in advance according to the present application is effective in reducing the load of the motion tracking correction.

Second Embodiment

An imaging apparatus according to the present embodiment differs from the imaging apparatus according to the first embodiment in that a divergence angle adjusting mechanism 116 that adjusts the emission angle of light emitted by the light source 106 is further provided. Herein, detailed descriptions of the content in the present embodiment that is similar to the content of the first embodiment will be omitted.

Figure 5A:
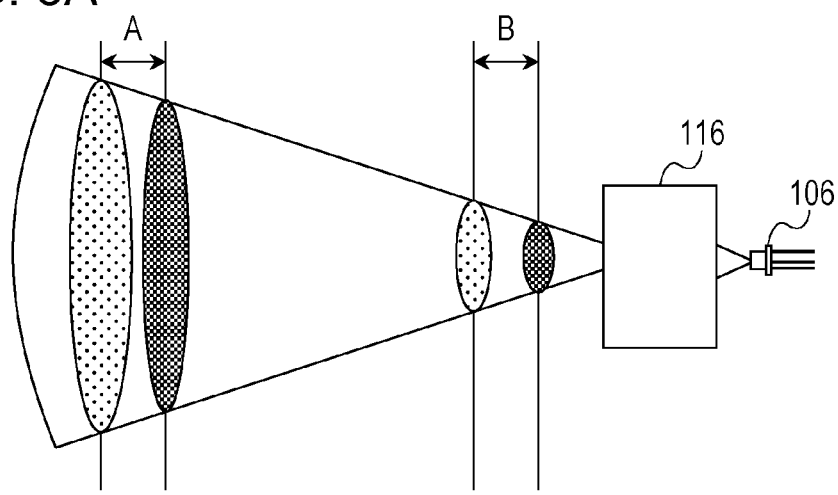
FIG. 5A illustrates a relationship between the divergence angle of a light source and a change in the density of irradiation light.
Figure 5B:
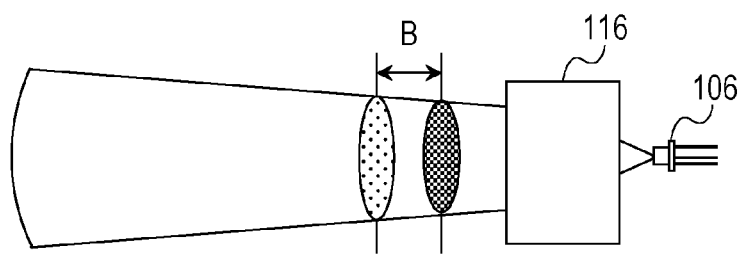
FIG. 5B illustrates a relationship between the divergence angle of a light source and a change in the density of irradiation light.
Figure 5C:
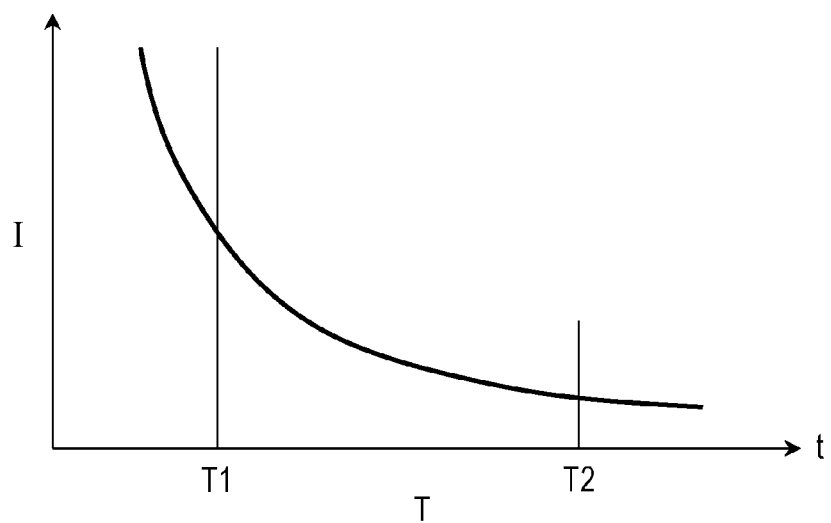
FIG. 5C illustrates a shutter start phase position that is appropriate under the conditions illustrated in FIGS. 5A and 5B.

FIG. 5A illustrates a relationship between the divergence angle of the light source and a change in the density of the irradiation light. The divergence angle adjusting mechanism 116 adjusts the divergence angle of the irradiation light emitted by the light source 106. For example, the divergence angle adjusting mechanism 116 is constituted by a diffusion plate and an optical lens or the like. When a case in which the subject 102 is at the position of A is compared with a case in which the subject 102 is at the position of B, the amount of change in the illuminance associated with the movement is inversely proportional to the distance from the light source, as indicated by the expression (2). Thus, the change in the intensity of an optical signal detected at the position A is smaller than the change in the intensity of an optical signal detected at the position B even when the amount of movement is the same. Therefore, as illustrated in FIG. 5C, the position at which the slope of the phase change of the optical signal detection intensity is relatively smaller becomes an optimal phase T2 at the position A, whereas the position at which the slope is relatively larger becomes an optimal phase T1 at the position B.

However, the optical signal 200 includes light with a long optical path length at the latest time, or for example, at t=t1 and includes light with a shorter optical path length toward t=t4, which is earlier in time. Therefore, as the shutter is started at a later time, the proportion of the information on a portion deep inside the subject 102 included in the optical signal 200 increases. Thus, in order to make the position at which the ratio of the cerebral blood flow component is high coincide with the optimal phase position in the movement correction, the divergence angle of the light source may be adjusted by using the divergence angle adjusting mechanism 116, as illustrated in FIG. 5B. In the case of FIG. 5B, the divergent angle is small as compared to (a-1), and thus the change in the illuminance associated with the movement of the subject 102 is small even at the position B. In other words, the optimal phase at the position B can be made to coincide with the optimal phase T2 at the position A in FIG. 5A (FIG. 5C). The divergence angle adjusting mechanism 116 may include a zoom lens mechanism. This makes it possible to monitor the distance to the subject 102 and to make an adjustment in real time in accordance with the distance, as appropriate. In addition, the absolute quantity of light decreases if the shutter start phase is too late, and the S/N ratio decreases. In this case, the divergence angle of the divergence angle adjusting mechanism 116 may be increased, and the optimal phase position may be brought temporally forward.

Third Embodiment

An imaging apparatus according to the present embodiment differs from the imaging apparatus according to the first embodiment in that a pattern projector 118 is provided at an exit surface of the light source 106. Herein, detailed descriptions of the content in the present embodiment that is similar to the content of the first embodiment will be omitted.

Figure 6A:
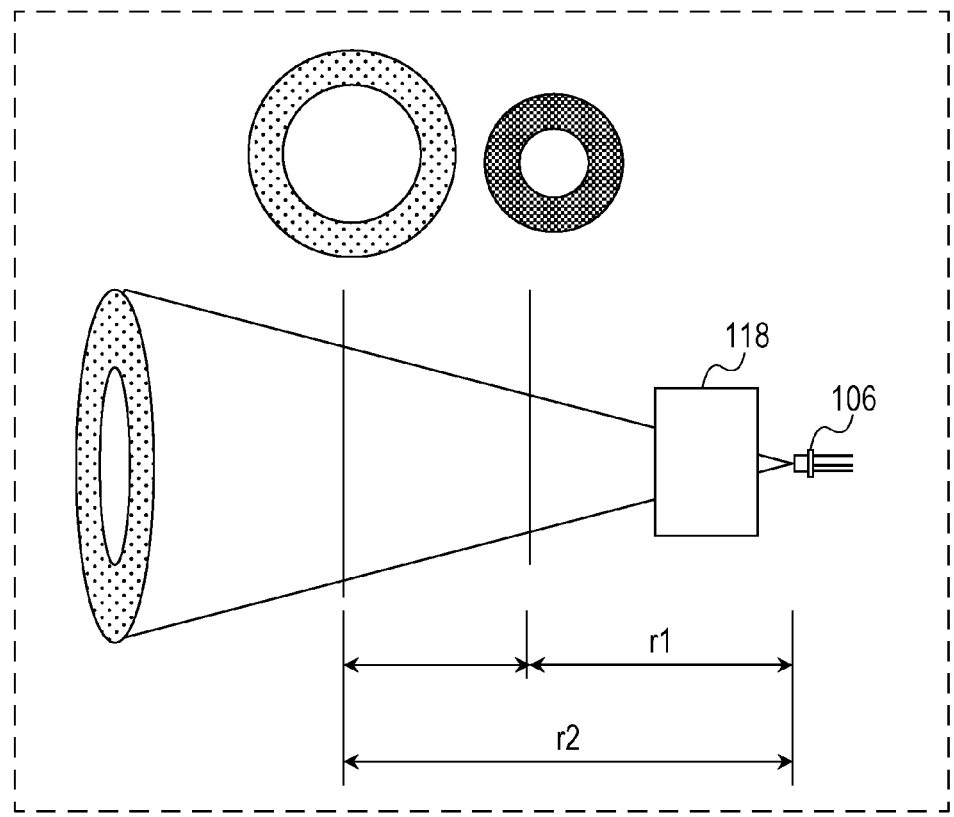
FIG. 6A illustrates an irradiation pattern example.
Figure 6B:
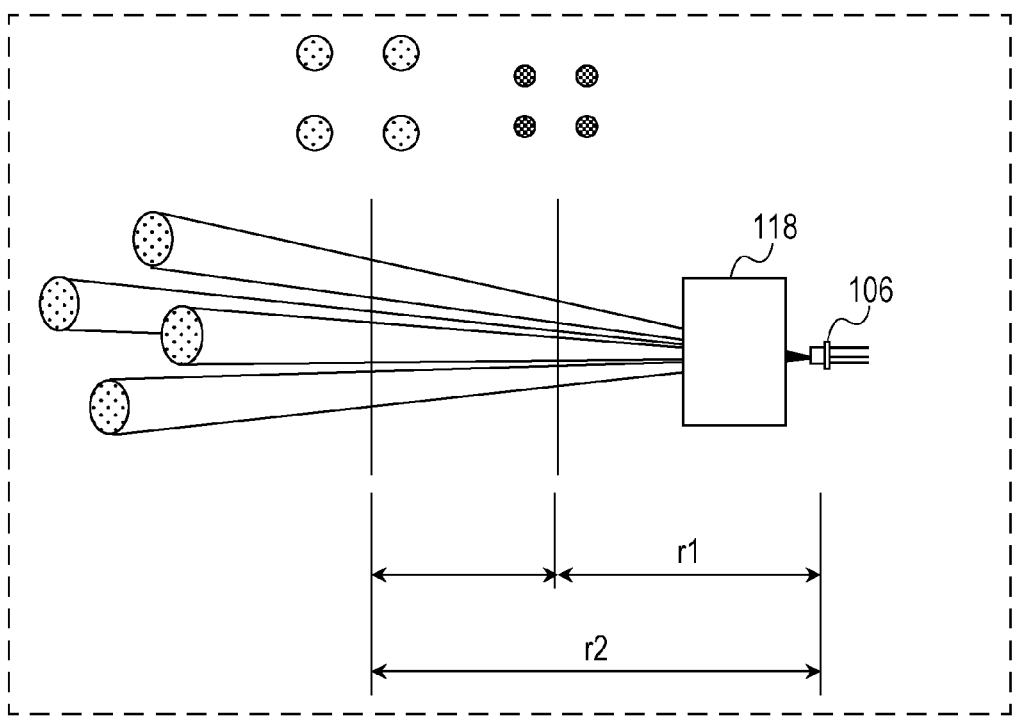
FIG. 6B illustrates an irradiation pattern example.

FIGS. 6A and 6B illustrate irradiation pattern examples formed by the pattern projector 118. In the imaging apparatus according to the first embodiment and the second embodiment, the light source 106 projects uniform illumination light. In contrast, in the present embodiment, light emitted by the light source 106 is converted to light having a ring-shaped pattern by the pattern projector 118 and is projected from the pattern projector 118. The portion at which the optical signal is detected in the projected irradiation pattern is inside the ring, or for example, the center of the ring. The ring-shaped pattern may have a constant ring width or may have a different ring width depending on the distance. FIG. 6B illustrates an example in which light having a dot-shaped pattern is projected from the pattern projector 118. The portion at which the optical signal is detected is between the dots. The dot-shaped pattern may have a constant dot diameter or may have a different dot diameter depending on the distance.

The pattern projector 118 includes a diffusion plate, an optical lens, a shading plate, and the like and converts the light to light having a desired pattern by blocking, converging, or reflecting a portion of the light emitted by the light source 106.

Fourth Embodiment

An imaging apparatus according to the present embodiment differs from the imaging apparatus of the other embodiments in that an arithmetic processor 120 is provided. Herein, detailed descriptions of the content in the present embodiment that is similar to the content of the first embodiment will be omitted.

The arithmetic processor 120 carries out processing of removing an offset component from a signal obtained by the photodetector 108. An offset component is a certain noise component that is contained when the returning light is detected no matter at which phase the shutter is started. The offset component is produced, for example, as a portion of an electric charge subjected to photoelectric conversion leaks into the electric charge accumulator 112 even in a state in which the accumulation of an electric charge from the photoelectric converter 110 to the electric charge accumulator 112 is being stopped. In addition, the offset component includes a component that passes through a space in a shading film that blocks light so as to cover the electric charge accumulator 112. When a large amount of offset component is generated, $\Delta I^{dis}$ decreases greatly as compared to $\Delta I^{ill}$, and thus the optimal phase position may shift greatly, or the optimal phase position may cease to be present. Therefore, the arithmetic processor 120 carries out the processing of separately estimating the offset component and subtracting through arithmetic processing.

Fifth Embodiment

In an imaging apparatus according to the present embodiment, the divergence angle of the irradiation light satisfies a certain conditional expression. Herein, detailed descriptions of the content in the present embodiment that is similar to the content of the first embodiment will be omitted.

Figure 7:
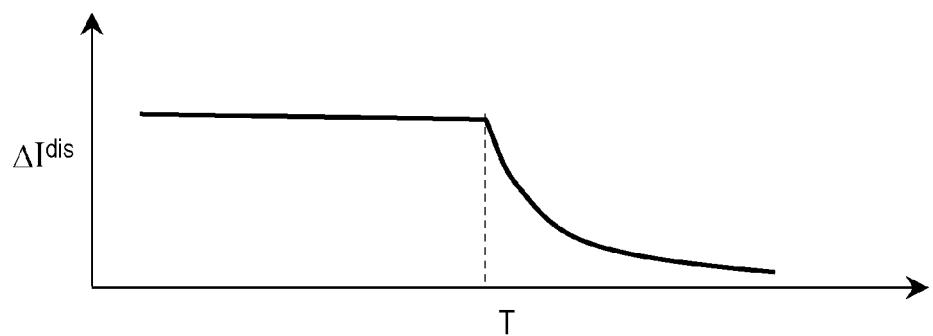
FIG. 7 illustrates a relationship between a shutter start phase and an amount of change in a detected optical signal associated with a variation in the flight distance of light.

FIG. 7 illustrates a relationship between a shutter start phase and an amount of change in a detected optical signal associated with a variation in the flight distance of light. In FIG. 7, the horizontal axis represents the shutter start phase, and the vertical axis represents the amount $\Delta I^{dis}$ of change in the detected optical signal associated with a variation in the flight distance of light. The variation in the flight distance of light corresponds to a variation in the time at which the light reaches the imaging apparatus 100. As illustrated in FIG. 7, when the light source 106 emits rectangular pulsed light, the amount $\Delta I^{dis}$ of change in the detected optical signal associated with a variation in the flight distance of the light is constant even if the shutter is started before the trailing end of the rectangular pulsed light. In addition, as illustrated in FIG. 7, when the shutter start phase is at a point after the trailing end of the rectangular pulsed light, the amount $\Delta I^{dis}$ of change in the detected optical signal associated with a variation in the flight distance of the light decreases along with an increase in the shutter start phase. Therefore, there is an upper limit to the amount $\Delta I^{dis}$ of change in the detected optical signal associated with a variation in the flight distance of the light.

In addition, when the shutter start phase is at a point after the beginning of the fall of the amount $\Delta I^{dis}$ of change in the detected optical signal associated with a variation in the flight distance of the light at the trailing end of the pulsed light, the imaging apparatus 100 can effectively acquire the internal scattering information of the subject 102. On the basis of the above, when the change in the quantity of detected light associated with the movement of the subject 102 is to be reduced by canceling the amount $\Delta I^{ill}$ of change in the detected optical signal resulting from a change in the illuminance of the irradiation light with the amount $\Delta I^{dis}$ of change in the detected optical signal associated with a variation in the flight distance of the light, the imaging apparatus according to the present embodiment at least satisfies the condition at which $\Delta I^{ill} \leq \Delta I^{dis}$ holds true.

Figure 8:
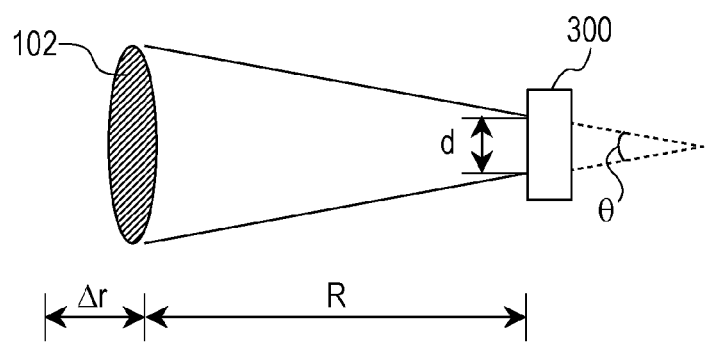
FIG. 8 illustrates a relationship between the divergence angle of irradiation light and the distance to a subject according to an embodiment.

FIG. 8 illustrates a relationship between the divergence angle θ of the irradiation light with which the light source 106 irradiates the subject 102 in the imaging apparatus 100 according to the present embodiment and the distance to the subject 102. The light source 106 includes a diffusion plate 300. The diameter of a spot of the irradiation light on the diffusion plate 300 is defined as d [mm], and the distance from the diffusion plate 300 to the subject 102 is defined as R [mm]. Then, the above condition $\Delta I^{ill} \leq \Delta I^{dis}$ is expressed as in the following expression (12).

$$\frac{1}{\frac{R+d/(2\tan\theta)}{2\Delta r}+1} \leq \exp\left(\alpha\frac{2\Delta r}{c}\right)-1 \quad (12)$$

In the above, c is the speed of light.

Here, as a measured result of an organism, $\alpha=2.7$ [1/ns], the speed of light $c=3\times10^8$ [m/s], and 10 [mm], which is an average body movement level of a human being, for $\Delta r$ are substituted. Then, the following expression (13) is derived.

$$81.5 \leq R+d/(2\tan\theta) \quad (13)$$

In the above, R, d, $\theta>0$ holds true.

Here, $\Delta r=10$ [mm] is substituted as a small distance variation, but this corresponds to an amount of variation when the subject himself/herself has paused consciously. As long as this condition is satisfied, there is a solution that can cancel the amount $\Delta I^{ill}$ of change in the detected optical signal resulting from a change in the illuminance of the irradiation light with the amount $\Delta I^{dis}$ of change in the detected optical signal associated with a variation in the flight distance of the light.

FIG. 9 illustrates an example of values obtained by subtracting the right-hand side from the left-hand side of the expression (13). Here, with d=5 mm, values obtained when the distance R from the diffusion plate 300 to the subject 102 and the divergence angle $\theta$ of the irradiation light serving as the parameters are calculated. Negative values in the table indicate that the expression (13) is not satisfied. With reference to FIG. 9, for example, it can be seen that, when the distance R to the subject 102 is 55 mm, if the divergence angle $\theta$ of the irradiation light is equal to or less than 4 degrees, the expression (13) is satisfied.

What is claimed is:

1. An imaging apparatus, comprising:
    a light source that includes a diffusion plate and, in operation, emits pulsed light toward a subject, the pulsed light diverging at a divergence angle greater than 0 degrees;
    a photodetector including a photoelectric converter that, in operation, receives light from the subject and converts the light to an electric charge, and an electric charge accumulator that, in operation, accumulates the electric charge, the photodetector, in operation, generating an electric signal based on the electric charge accumulated in the electric charge accumulator; and
    a control circuit that, in operation, controls the light source and the photodetector, wherein:
    the control circuit, in operation, causes the electric charge accumulator to start accumulating the electric charge when a predetermined period of time has passed after the control circuit has caused the light source to start emitting the pulsed light, and thus causes the electric charge accumulator to accumulate the electric charge corresponding to a component, among the light from the subject, that is scattered inside the subject, and
    the pulsed light satisfies the following expression:
    $81.5 \leq R+d/(2\tan\theta)$, where R (mm) is a distance from the diffusion plate to the subject, $\theta$ (degree) is the divergence angle, and d (mm) is a spot size of the pulsed light on the diffusion plate.

2. The imaging apparatus according to claim 1, further comprising:
    a divergence angle adjusting mechanism that, in operation, adjusts the divergence angle.

3. The imaging apparatus according to claim 1, further comprising:
    a pattern projector that, in operation, converts the pulsed light to light including a desired pattern.

4. The imaging apparatus according to claim 1, wherein:
    the electric signal includes a predetermined offset component, and
    the control circuit, in operation, removes the predetermined offset component from the electric signal.

5. The imaging apparatus according to claim 1, wherein the distance from the diffusion plate to the subject is equal to or greater than 25 mm, and is equal to or less than 400 mm.

* * * * *